US008323623B2

(12) United States Patent
Klocke et al.

(10) Patent No.: US 8,323,623 B2
(45) Date of Patent: Dec. 4, 2012

(54) PHARMACEUTICAL MOIRÉ PILL

(75) Inventors: Stefan Klocke, Karlsruhe (DE); Harald Walter, Zurich (CH); Alexander Stuck, Wettingen (CH)

(73) Assignee: I-Property Holding Corp., Sarasota, FL (US)

( * ) Notice: Subject to any disclaimer, the term of this patent is extended or adjusted under 35 U.S.C. 154(b) by 20 days.

(21) Appl. No.: 12/762,107

(22) Filed: Apr. 16, 2010

(65) Prior Publication Data

US 2011/0256069 A1 Oct. 20, 2011

Related U.S. Application Data

(63) Continuation of application No. PCT/US2008/011868, filed on Oct. 17, 2008.

(60) Provisional application No. 61/105,839, filed on Oct. 16, 2008, provisional application No. 60/980,668, filed on Oct. 17, 2007.

(51) Int. Cl.

| | |
|---|---|
| ***A61K 9/44*** | (2006.01) |
| ***A61K 9/28*** | (2006.01) |
| ***B27N 3/18*** | (2006.01) |
| ***B29C 35/08*** | (2006.01) |
| ***B41J 2/01*** | (2006.01) |

(52) U.S. Cl. ...... 424/10.2; 427/2.14; 264/319; 264/400; 347/104

(58) Field of Classification Search ........ 424/10.1–10.2; 264/319, 400; 347/104; 427/2.14
See application file for complete search history.

(56) References Cited

U.S. PATENT DOCUMENTS

| | | | | |
|---|---|---|---|---|
| 3,557,262 | A * | 1/1971 | Mitchell et al. | 264/37.32 |
| 2006/0129489 | A1 * | 6/2006 | Hersch et al. | 705/50 |

FOREIGN PATENT DOCUMENTS

| | | | |
|---|---|---|---|
| WO | 03005839 | | 1/2003 |
| WO | 2006047695 | | 5/2006 |
| WO | WO 2006/047695 | * | 5/2006 |

OTHER PUBLICATIONS

International Search Report Forms: PCT/ISA/220, PCT/ISA/210, PCT/ISA/237, mailing date of Feb. 9, 2009.

* cited by examiner

*Primary Examiner* — Ileana Popa
*Assistant Examiner* — Genevieve S Alley
(74) *Attorney, Agent, or Firm* — Wood, Herron & Evans, LLP

(57) ABSTRACT

A pharmaceutical dosage form [11, 11*g*] has reduced susceptibility to counterfeiting, due to the forming directly thereon of a pattern or base layer [10, 10*g*] of a Moiré pair, wherein a Moiré effect is visually observable by looking through a revealing layer [12, 12*g*] positioned closely to and superimposed on the base layer [10, 10*g*]. The pattern fanned on the pharmaceutical dosage form [11, 11*g*] may be formed by embossing, oblation, inkjet printing, or tampon printing. The revealing layer [12, 12*g*] of the Moiré pair can be part of a blister package containing the pharmaceutical dosage form [11, 11*g*], so that the Moiré effect is observable while looking at the pharmaceutical dosage form [11, 11*g*] as it remains within the package.

13 Claims, 4 Drawing Sheets

PHARMACEUTICAL MOIRÉ PILL

This application claims priority, under Section 371 and/or as a continuation under Section 120, to PCT Application No. PCT/US2008/011868, filed on Oct. 17, 2008, which claims priority to U.S. Provisional Patent Application No. 61/105,839, filed on Oct. 16, 2008, and also to U.S. Provisional Patent Application No. 60/980,668, filed on Oct. 17, 2007.

FIELD OF THE INVENTION

This invention relates to composite dosage forms such as pharmaceutical compositions and components thereof. More particularly, this invention relates to composite dosage forms comprising one or more features that provide anti-counterfeiting characteristics to such dosage forms. In more detail this invention relates to dosage faints comprising a Moiré pattern directly in or on a surface or interface of the dosage form.

BACKGROUND OF THE INVENTION

Forged, grey market, and illegal re-imports are of increasing concern in the pharmaceutical industry. This is not only a topic in the third world, where the fraction of counterfeit pharmaceutical products in the supply chain is sometimes above 50%. This problem has now reached the second and first worlds likewise, especially as pharmaceuticals are often much more expensive in these areas. AIDS and cancer drugs are sometimes subsidized in developing countries, which enhances the danger of illegal re-imports.

Anti-counterfeiting strategies currently in use in the pharmaceutical industry have so far not been very successful in preventing forgery, illegal re-imports and other activities commonly summarized as counterfeiting. Anti-counterfeiting features in the pharmaceutical market nowadays are generally only applied to packages. Holograms, optically variable inks, fluorescent dyes, special printing techniques like micro-printing, and other security features are attached to the packages by use of adhesive tags, or these are laminated to the carton, or they are directly applied to the packages. The main drawback of such labels is that they can be removed from the product or the packaging and reused or analyzed. Some companies offer security features applied to the sealing foil of blister packages, but these features possess the same disadvantages.

No secure labeling of the pharmaceutical material itself, e.g., of solid dosage forms such as pills, is in the market yet. Techniques that use forgery-resistant signatures, such as DNA of known sequence (U.S. Pat. No. 5,451,505) or molecules with characteristic isotopic composition or micro-particles with characteristic color layer sequence (U.S. Pat. No. 6,455,157 B1) are not applicable here, as these signatures incorporate biologically active components that are consumed with the pharmaceutical material. Certification authorities, such as the Food and Drug Administration (FDA) in the U.S., have not granted approval for such anti-counterfeiting solutions. Only a few ideas of applying a hologram to edible products have been published. One is based on coating an edible product with a thermo-formable and thus embossable layer (WO 01/10464 A1). As this layer alters the composition of the product, as well as the production process, a new approval of the drug from certification authorities would be needed. Further the heating during the thermo-forming steps can harm many active agents. In another approach a polymer solution is brought into contact with a diffraction relief mold and then hardened upon drying (U.S. Pat. No. 4,668,523). The drying step can be accelerated by heating, and in the end the hardened edible polymer product possesses the diffractive relief of the mold. This method is limited to polymer solutions, it is very slow, and the heating step can be harmful to active agents used in pharmaceutical products, as it may negatively affect the activity of the active pharmaceutical agents.

One significant opportunity in designing pharmaceutical dosage forms is that of product identification and differentiation. It is useful, both from a consumer safety perspective and from a commercial perspective, to have a pharmaceutical dosage form with a unique appearance that is readily recognizable and identifiable.

One currently used technique for providing unique dosage form identification includes the use of intagliations. Intagliations are impressed marks typically achieved by engraving or impressing a graphical representation, for example a figure, mark, character, symbol such as a letter, a name, a logo, a pictoral representation, and the like, or any combination thereof; in a tablet or other solid dosage form, such as by a punching procedure. U.S. Pat. No. 5,827,535, for example, describes soft gelatin capsules with an external surface having defined thereon an impressed graphical representation. U.S. Pat. No. 5,405,642 discloses a method of highlighting intagliations in white or color-coated tablets by spraying onto said tablets a suspension comprising a filling material having a different color, a waxy material and a solvent, then removing the solvent and the excess filling and waxy material. However, it is often difficult to maintain the waxy material in an amount sufficient to promote suitable bonding of the filling material, yet be suitably removable with solvent.

EP 088,556 relates to a method of highlighting intagliations in white or colored tablets by contacting said tablets with a dry, powdery material having a different color than that of the tablet surface, then removing the excess powdery material not deposited in the intagliations. Disadvantageously, it has been found that the adhesion of the powdery material to the intagliations is not satisfactory, as the material shows a tendency to loosen and fall out.

EP 060,023 discloses a method of emphasizing intagliations in colored (i.e., not white) solid articles, in particular tablets, by coating the tablet surface and filling up the intagliations with a coating film comprising an optically anisotropic substance. An optical contrast between the tablet surface and the intagliations is obtained, presumably due to different orientation of the optically anisotropic substance on the tablet surface and in the intagliations. However, this technique is limited to colored articles and only allows for the use of optically anisotropic filling materials.

Labeling fluorescing pharmaceutical products by jetting an inkjet a non fluorescing material onto the UV-fluorescing substrate of the product is known from the EP1640421A1. Printed images are created when an UV light is applied to the product. The fluorescent product fluoresces while the non-UV fluorescent inkjet printed area does not. To visualize the labels UV light is needed.

Another way to identify and differentiate one dosage form from another is via application of microreliefs to the dosage form. See, e.g. U.S. Pat. No. 4,668,523 and WO 01/10464 (microreliefs in the outer surface of dosage form). A microrelief is a regular pattern of ridges and grooves and the like that may display a visual effect or optical information when exposed to suitable light. Disadvantageously, production difficulties could be encountered when using these methods to stamp microrelief patterns into tablets having irregular shapes and/or surfaces.

WO 2006/047695 shows a variety of methods to manufacture pharmaceutical dosage forms showing different kinds of microreliefs embedded into their surface. However, based on further review, it seems that the solutions proposed by WO 2006/047695 result in microreliefs that are not recognizable by the human eye. In particular, overcoating of microstructures usually makes them invisible because most overcoatings have a similar optical index of refraction as the pharmaceutical dosage form completely eliminating optical reflections from the interface between the two.

The use of the moiré effect in security features for object of value is known in the art. E.g. US2007/0177131A1 teaches moiré pattern in a first layer on credit cards, banknotes or identity cards, the pattern being verified by superposing the first layer with a moiré analyzer in a second layer. The first layer with the moiré pattern is disposed on a carrier layer. Both are fixed to the object of value or the package. The first layer can be removed from the object and reused on a different object which is critical especially for identity documents.

SUMMARY OF THE INVENTION

The present invention relates to a solid pharmaceutical dosage form (hereinafter also called "pill"), the surface or an interface of which is patterned in such a way that if the dosage form is viewed through a revealing layer, a moiré or Glass pattern effect appears. The moiré pattern is manufactured directly on or in the surface or an interface of the dosage form. No carrier layer and the like are needed. This gives a high level of security as the pattern cannot be removed from the dosage form without destroying it. This is the case especially if the moiré pattern is located at the interface between the core of the dosage form and a transparent or semitransparent coating. The revealing layer may be transparent with a printed and/or embossed part. It may be part of the blister package or other package of the pill or pills. It may also be supplied independently of the pill and its package or be part of an electronic imaging system.

The applicant found that only dry-compression techniques using certain pressure parameters can be employed in order to reliably obtain microreliefs in pharmaceutical dosage forms in addition, the use of certain dyes is necessary, as the resulting colors have a contrast effect that makes recognition of microreliefs possible for the human eye. The applicant is filing a parallel application that shows some of the necessary parameters in the case of the present invention it is important to note that the invention proposes a moiré effect that requires the use of a revealing layer that is fundamentally distinct from the dosage form itself. This invention is therefore using a different approach than that proposed in WO 2006/047695.

These and other features of the invention will be more readily understood in view of the following detailed description and the drawings.

DETAILED DESCRIPTION OF THE PREFERRED EMBODIMENTS

Figure 1A:
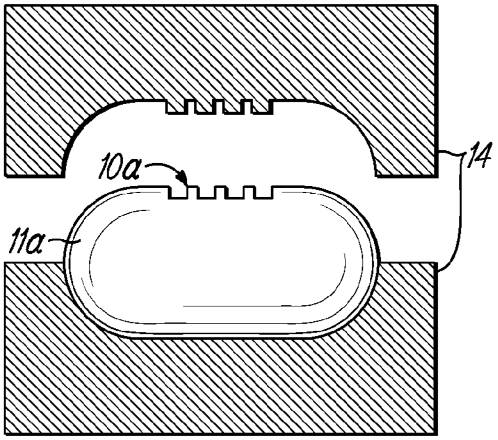
FIGS. 1A, 1B, 1C, and 1D are schematics which show four different techniques for forming the base layer of a Moiré pattern on or in the surface of an interface of a pharmaceutical dosage form, according to the invention.
Figure 1B:
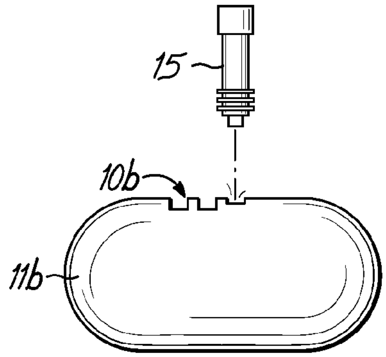
Figure 1C:
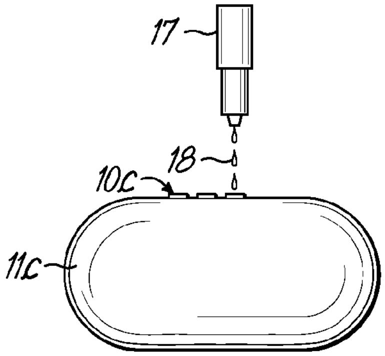
Figure 1D:
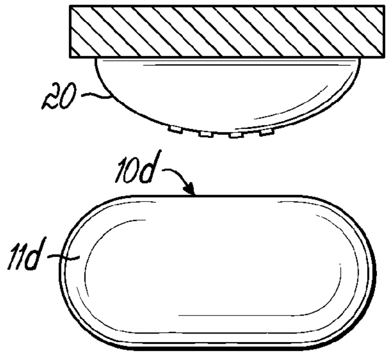

In order to prepare a solid dosage form containing one or more active ingredients (such as drugs), it is necessary that the material to be compressed into the dosage form possess certain physical characteristics that lend themselves to processing in such a manner. Among other things, the material to be compressed must be free-flowing, must be lubricated, and importantly must possess sufficient cohesiveness to insure that the solid dosage form remains intact after compression.

In the case of tablets, the tablet is formed by pressure being applied to the material to be tabletted on a tablet press. A tablet press includes a lower punch that fits into a die from the bottom and an upper punch having a corresponding shape and dimension that enters the die cavity from the top after the tabletting material fills the die cavity. The tablet is formed by pressure applied on the lower and upper punches. The ability of the material to flow freely into the die is important in order to insure that there is a uniform filling of the die and a continuous movement of the material from the source of the material, e.g., a feeder hopper. The lubricity of the material is crucial in the preparation of the solid dosage forms because the compressed material must be readily ejected from the punch faces.

Because most drugs have none or only some of these properties, methods of tablet formulation have been developed in order to impart these desirable characteristics to the material (s) to be compressed into a solid dosage form. Typically, the material to be compressed into a solid dosage form includes one or more excipients that impart the free-flowing, lubrication, and cohesive properties to the drug(s) being formulated into a dosage form.

Lubricants are typically added to avoid the material(s) being tabletted from sticking to the punches. Commonly used lubricants include magnesium stearate and calcium stearate. Such lubricants are commonly included in the final tabletted product in amounts of less than 1% by weight.

In addition to lubricants, solid dosage forms often contain diluents. Diluents are frequently added in order to increase the bulk weight of the material to be tabletted in order to make the tablet a practical size for compression. This is often necessary where the dose of the drug is relatively small.

Another commonly used class of excipients in solid dosage forms are binders. Binders are agents that impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethylcellulose.

There are two general methods of preparation of the materials to be included in the solid dosage form prior to compression: (1) dry granulation and (2) wet granulation.

Dry granulation procedures may be used where one of the constituents, either the drug or the diluent, has sufficient cohesive properties to be tabletted. The method includes mixing the ingredients, slugging the ingredients, dry screening, lubricating, and finally compressing the ingredients.

The wet granulation procedure includes mixing the powders to be incorporated into the dosage from in, e.g., a twin shell blender or double-cone blender and thereafter adding solutions of a binding agent to the mixed powders to obtain solutions of a binding agent to the mixed powders to obtain, a granulation. Thereafter the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

In direct compression, the powdered material(s) to be included in the solid dosage form is compressed directly without modifying the physical nature of the material itself. The use of direct compression is limited to those situations where the drug or active ingredient has a requisite crystalline structure and physical characteristics required for formation of a pharmaceutically acceptable tablet. On the other hand, it is well known in the art to include one or more excipients that make the direct compression method applicable to drugs or active ingredients that do not possess the requisite physical properties. For solid dosage forms in which the drug itself is to be administered in a relatively high dose (e.g., the drug itself comprises a substantial portion of the total tablet weight), it is necessary that the drug itself have sufficient physical characteristics (e.g., cohesiveness) for the ingredients to be directly compressed. In any case, applicant found that direct compression techniques are feasibly in order to reliably obtain microreliefs such as Moiré gratings in pharmaceutical dosage forms that would then also result in an optical effect being recognizable for the human eye. Embossing the moiré pattern in the dosage form during the compression process offers the highest level of security. Alternatively the patterns can be manufactured in the compressed dosage form by ablation techniques such as laser ablation or by printing techniques. Preferred printing techniques are ink jet printing or tampon printing or screen printing. Suitable inks for printing on pharmaceutical dosage forms are e.g. TiO2 or bone black. Such inks have to be nontoxic and they need an approval from an authority like the FDA (Food and drug administration in USA).

FIG. 1 shows schematically four different methods to realize the base layer 10 of a moiré pattern in the surface or at an interface of pharmaceutical dosage forms 11. More particularly, FIG. 1A shows a pharmaceutical dosage form 11*a*, in which the base layer 10*a* of a Moiré pattern is formed via compression from a pair of opposing mold halves 14. FIG. 1B shows a laser 15 used to form the base layer 10*b* of a Moiré pattern on pharmaceutical dosage form 11*b*. FIG. 1C shows an inkjet head 17 supplying ink droplets 18 to pharmaceutical dosage form 11*b* to form the base layer of a Moiré pattern 11*c*. And FIG. 1D shows a tampon printing device 20 used to imprint the base layer 10*d* of a Moiré pattern on pharmaceutical dosage form 11*d*.

In a preferred embodiment the core of a dosage form 11*a* is compressed with the direct compression technique. An example of a compressing mass mixture is shown in table 1.

TABLE I

Example of compressing mass mixtures

| Fraction | Ingredients |
|---|---|
| 70-80% | Lactose Monohydrate |
| 10-25% | Microcrystalline Cellulose |
| <10% | Aerosil (colloidal silica, anhydrous), Magnesium-stearat (Mg-stearate), polyethyleneglycol, color and active agent |

Figure 2A:
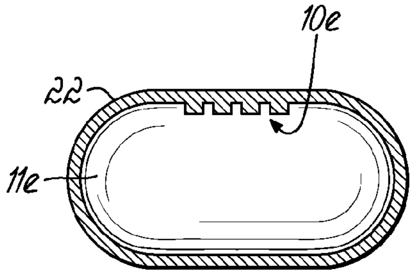
FIGS. 2A and 2B are schematics which show an embodiment of the invention, wherein the base layer of a Moiré pattern resides within a semi-transparent coating.
Figure 2B:
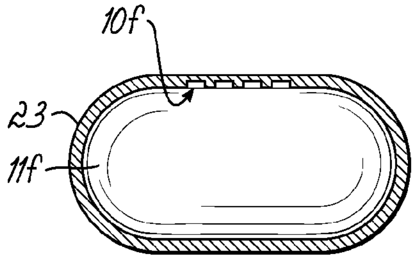

The Moiré pattern is manufactured on or in this core by one of the techniques shown in FIG. 1. Afterwards the patterned core of the dosage form is coated with a transparent (e.g. PVA) or semitransparent coating, the coating having a contrast in the optical properties with respect to the compressed core. FIG. 2 schematically shows dosage forms manufactured according to this preferred embodiment. In this embodiment the Moiré pattern is located at an interface of the dosage form. More particularly, FIGS. 2A and B schematically show the base layers of Moiré patterns 10*e*, 10*f*, residing at the interface between the corresponding pharmaceutical dosage forms 11*e*, 11*f*, and the transparent coatings 22, 23, respectively.

Typically, however, excipients are added to the formulation to impart good flow and compression characteristics to the material as a whole that is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dehydrate, among others.

A processed cellulose, microcrystalline cellulose, has been used extensively in the pharmaceutical industry as a direct compression vehicle for solid dosage forms. Microcrystalline cellulose is commercially available under the tradename, "EMCOCEL®® from Edward Mendell Co., Inc., and as Avicel® from FMC Corp. Compared to other directly compressible excipients, microcrystalline cellulose is generally considered to exhibit superior compressibility and disintegration properties.

Suitable polymers for inclusion in top coatings include polyvinylalcohol (PVA); water soluble polycarbohydrates such as hydroxypropyl starch, hydroxyethyl starch, pullulan, methylethyl starch, carboxymethyl starch, pre-gelantinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; polyvinylpyrrolidone and polyvinylacetate copolymers; and derivatives and combinations thereof. Suitable film-forming water insoluble polymers for inclusion in top coatings include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable film-forming pH-dependent polymers for inclusion in top-coatings include enteric cellulose derivatives, such as for example hydroxypropyl methylcellulosephthalate, hydroxypropyl methylcellulose acetate succinate, cellulose acetate phthalate; natural resins, such as shellac and zein; enteric acetate derivatives such as for example polyvinylacetate phthate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, "EUDRAGIT S;" and poly(methacrylic acid, methyl methacrylate) 1:1, which is commercially available from Rohm Pharma GmbH under the tradename "EUDRAGIT L;" poly (butyl, methacrylate (dimethylaminoethyl)methacrylate, methyl methacrylate), which is commercially available from Rohm Pharma GmbH under the tradename, "EUDRAGIT E;" and the like, and derivatives, salts, copolymers, and combinations thereof.

In one embodiment, the top coating includes coatings having a high rigidity, i.e., e.g., those coatings having a yield value sufficient to prevent deformation of the microrelief when exposed to normal manufacturing, handling, shipping, storage, and usage conditions. Suitable top coatings having high rigidity include film formers, such as for example, the high tensile strength film-formers well known in the art. Examples of suitable high tensile strength film-formers include, but are not limited to, methacrylic acid and methacrylate ester copolymers; polyvinylpyrrolidone; cellulose acetate; hydroxypropylmethylcellulose (HPMC), polyethylene oxide and polyvinylalcohol, which is commercially available from BASF under the tradename, "Kollicoat IR;" ethylcellulose; polyvinyl alcohols; and copolymers and mixtures thereof.

In one embodiment, the top coatings may include the water-soluable high rigidity film formers selected from HPMC, polyvinylpyrrolidone, the aminoalkyl-methacrylate copolymers marketed under the trade mark, "EUDRAGIT E;" and copolymers and mixtures thereof.

The inventive dosage form may come in a variety of different shapes. For example, in one embodiment the dosage form may be in the shape of a truncated cone. In other embodiments the dosage form may be shaped as a polyhedron, such as a cube, pyramid, prism, or the like; or may have the geometry of a space figure with some non-fiat faces, such as a cone, cylinder, sphere, torus, or the like. Exemplary shapes that may be employed include tablet shapes formed from compression tooling shapes described by "the Elizabeth Companies Tablet Design Training Manual" (Elizabeth Carbide Die Co., Inc., p. 7 (McKeesport, Pa.) (incorporated herein by reference). The tablet shape corresponds inversely to the shape of the compression tooling.

In embodiments in which the dosage form is prepared via compression, suitable fillers include, but are not limited to, water-soluble compressible carbohydrates such as sugars, which include dextrose, sucrose, isomaltalose, fructose, maltose, and lactose, polydextrose, sugar-alcohols, which include mannitol, sorbitol, isomalt, maltilol, xylitol, erythritol, starch hydrolysates, which include dextrins, and maltodextrins, and the like, water insoluble plastically deforming materials such as microcrystalline cellulose or other cellulosic derivatives, wetter-insoluble brittle fracture materials such as dicalcium phosphate, tricalcium phosphate, and the like and mixtures thereof.

In embodiments in which the dosage form is prepared via compression, suitable binders include, but are not limited to, dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, Whelan, rhamsan, zooglan, methylan, chitin, cyclodextrin, chitosan, polyvinyl pyrrolidone, cellulosics, starches, and the like; and derivatives and mixtures thereof.

In embodiments in which the dosage form is prepared via compression, suitable disintegrants include, but are not limited to, sodium starch glycolate, cross-lined polyvinylpyrrolidone, cross-linked carboxymethylcellulose, starches, microcrystalline cellulose, and the like.

In embodiments in which the dosage form is prepared via compression, suitable lubricants include, but are not limited to, long chain fatty acids and their salts, such as magnesium stearate and stearic acid, talc, and waxes.

In embodiments in which the dosage form is prepared via compression, suitable glidants include, but are not limited to, colloidal silicon dioxide, and the like.

In embodiments in which the dosage form is prepared via compression, the dosage form of the invention may also incorporate pharmaceutically acceptable adjuvants, including but not limited to preservatives, high-intensity sweeteners such as aspartame, acesulfame potassium, cyclamate, saccharin, sucralose, and the like; and other sweeteners such as dehydroalcones, grycyrrhizin, Monellin™, stevioside, Talin™, and the like; flavors, antioxidants, surfactants, and coloring agents.

The moiré effect is a visual perception that occurs when a set of lines or dots on a base layer are optically superimposed with another set of lines or dots, the revealing layer, where the two sets differ in relative size, angle, and/or spacing. The base layer together with the revealing layer is called moiré pair within this document. The moiré effect can be generated by photographic or electronic reproduction, embossing and/or printing or by lithographic structures.

Figure 3:
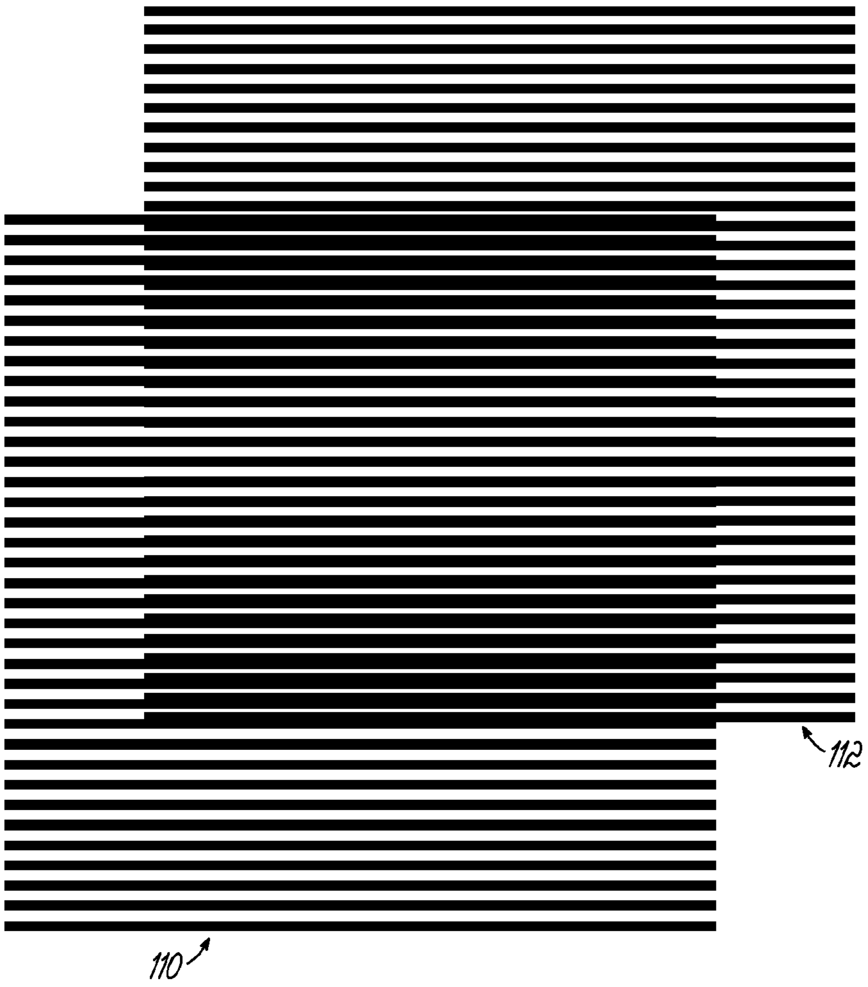
FIG. 3 shows another aspect of the invention, via the superposition of two linear patterns to form a simple Moiré effect.

Simple moiré patterns are observed when superposing two layers comprising periodically repeating opaque parallel lines with similar spacing as shown in FIG. 3. For example, FIG. 3 shows a base layer 110 of a simple Moiré linear pattern, with a revealing layer 112 partially superimposed thereover. In this case the lines of the base and the revealing layer are parallel to each other. The superposition image of FIG. 3 outlines periodically repeating dark parallel bands, called moiré lines. The spacing between the moiré lines is much larger than the periods of lines in the two layers. If $s_b$ is the spacing of the lines in the base layer and $s_r$ the spacing of the lines in the revealing layer than the spacing $s_l$ between the moiré lines is as follows:

$$s_l = s_b \cdot s_r / |(s_b - s_r)| \quad (1)$$

Resolving equation 1 for example for $s_b$=100 μm and $s_r$=95 μm gives $s_l$=1.9 mm which can be easily seen by the human eye. Light bands of the superposition image correspond to the zones where the lines of both layers overlap. The dark bands of the superposition image forming the moiré lines correspond to the zones where the lines of the two layers interleaf, hiding the light background. In this simple case, the light and dark zones are periodically interchanging. The superposition image does not change if transparent layers with their opaque patterns are inverted.

Moiré pattern appear even if the spacing are equal ($s_b$=$s_r$=s) when the lines are rotated by an angle α with respect to each other. The spacing s of the moiré lines can be calculated according to equation 2.

$$s_l = s/(2 \cdot \sin(\alpha/2)) \quad (2)$$

FIG. 3*b* shows an example of such a moiré pattern.

Preferred values for $s_b$ and $s_r$ are in the range of 10 μm up to 1 mm, especially preferred between 30 μm and 500 μm and in particular preferred between 50 μm and 300 μm.

When considering pharmaceutical dosage forms according to this invention, the pill acts as the base layer. For this the Moiré pattern has to be manufactured directly on or in the pill in an FDA conformal manner. Gluing or laminating a base layer is not appropriate. The revealing layer is printed and/or embossed in or on a transparent material, like for example a bulk piece of glass or plastic, a plastic foil, a lacquer layer, a laminated foil, a perforated thin paper, or the like. The characteristic distances of the two layer patterns are close. Preferred the distance is in the range of a few tenth of micrometer up to some tenth of millimeter. An observer sees the moiré pattern by looking through the revealing layer, which is positioned closely to the base layer, i.e., the pharmaceutical pill. The revealing layer may also be an electronic camera system, onto which the pattern of the base layer is imaged. The pattern of the revealing layer is then electronically superimposed on the image of pill surface to reveal the moiré pattern.

Independently of how the moiré pattern is revealed, the base pattern must be implemented into the pill surface or interface in such a way as to make an optical contrast. Preferred the pattern is embossed during the compression process as this method offers the highest level of security. Alternatively the pattern is realized by ablation techniques, e.g. laser ablation, printing, especially tampon or inkjet printing, or other suitable technique. In case of an embossed pill the optical contrast is caused by locally varying surface geometries, which reflect and scatter incident light differently from place to place. In order to make a moiré pattern, at least 2 different reflective or diffuse structures need to be embossed into the pill at the same time.

Visible contrast of the base layer pattern is achieved by direct embossing of a micro- and/or nanostructure. A punching tool with a micro- and/or nanostructured surface directly compresses a pharmaceutical formulation in a press. Under the proper manufacturing conditions a very fast transfer of the tool surface geometry into the surface of the pharmaceutical dosage form is achieved. In combination with the inherent reflection and absorption properties (color) of the form material the modified surface geometry changes the local optical appearance of the surface, creating a well visible optical contrast. Depending on the precise surface geometry a single or a combination of several optical mechanisms are responsible for contrast formation: interference, diffuse single and/or multiple scattering, single and/or multiple reflection and single and/or multiple absorption of visible light. As long as the microstructure is smaller or close to the resolution limit of the human eye, i.e. smaller than about 100 micrometers, only the optical effects of the microstructure, i.e. a contrast is perceived by humans. The microstructure itself is not seen by the unaided eye.

Micro- and nanostructures which enhance multiple reflections on colored pills create a visible color contrast because only wavelengths with high reflectivities are reflected several times, other wavelengths are absorbed. Light from multiple reflections is therefore narrowly centered around the wavelength with maximal reflectivity. Geometrically structuring a surface to favour multiple reflections within the surface therefore shifts the average reflected wavelength towards the wavelength with maximum reflectivity. If several dyes are used in a given pill, the color is shifted towards the wavelength with the highest reflectivity by embossing a suitable micro- or nanostructure into the surface, giving a visible color contrast. Other possible contrast mechanisms are satiation, darkening by reducing reflectivities and diffraction by grating structures. By locally changing the microstructure in the compression tool, the base layer pattern is therefore formed in a single manufacturing step.

The applicant has found that the inventive solution will only work if certain pressure parameters are used during embossing The powder mixture is compressed between two punches, which apply axial mechanical forces in the range of 5-40 kN, but depend on the size of the pill in question. Compression reduces the volume of the mass and at the same time increase its mechanical strength. The compression process is essentially a high-impact molding process and works at room temperature without heating. State-of-the-art single rotary presses work at high speed and produce about 30,000 to 300,000 pills per hour. This means that compression tune per pill is well below 100 ms. This time is long enough to compress the raw powder material to a hard pill, but the pill is still soluble after it is ingested.

Figure 4:
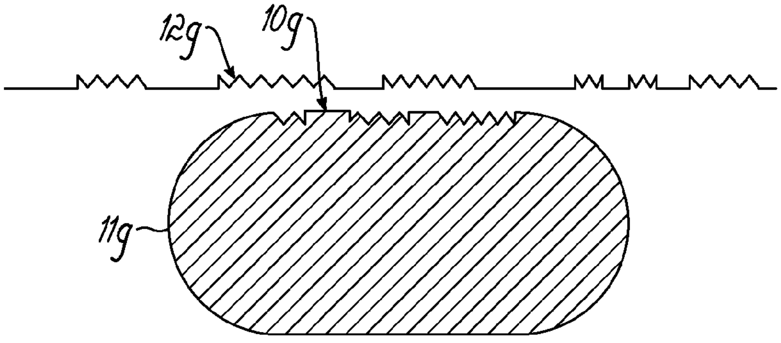
FIG. 4 is a schematic that shows a specific example of one practical use of a Moiré pattern.

In a preferred embodiment of this invention, the pressure parameters of the tablet press are set in a way that correlates with the mixture of ingredients used in the particular pharmaceutical dosage form. However, it was found that pressure parameters generally have to be set at the upper end of the spectrum of commercially available tablet presses, good results for a flat pill with a diameter of 11 mm were obtained for compression forces between 15 and 35 kN. This resulted in pills with a hardness between 100-250 N. In certain embodiments of the invention the tablet press parameters were set in a range of between 10 and 50 kN, FIG. 4 is a schematic which better illustrates a principle of the invention, and may be applicable to the packaging of a pharmaceutical dosage form 11. More particularly, the dosage form 11*g* has a base layer 10*g* formed thereon, with a revealing layer 12*g* located relative to the base layer 10*g*, i.e. superimposed above and in alignment therewith. If the base layer 10*g* is an image contrast generated by the pharmaceutical dosage form 11*g*, and the revealing layer 12*g* is part of the blister package for the pharmaceutical dosage form 11*g*, the Moiré pattern will be visible to the human eye by viewing the pharmaceutical dosage form 11*g* through the blister pack, while still in the package.

Figure 5A:
FIGS. 5A, 5B, 5C, and 5D, schematically show different examples of optical structures forming an optical contrast in the surface of a pharmaceutical dosage form, according to additional aspects of the invention.
Figure 5B:
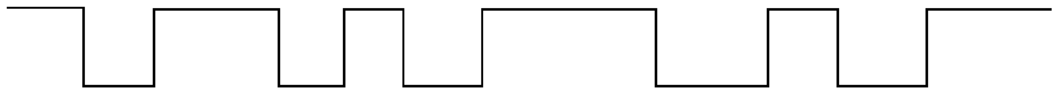
Figure 5C:
Figure 5D:

Other possible examples of base layer pattern structures are shown in FIG. 5A-5D, including two different embossed random patterns (FIG. 5A and FIG. 5B), wherein the structure may have an average lateral size between 0.5 microns and 10 microns and an average depth between 50 nm and 5 microns. Beneath that, in FIG. 5C, a two level structure is shown, wherein a smaller pattern is formed within the recesses of square-shaped or rectangularly-shaped depressions, where the edges may generate the optical contrast. FIG. 5D shows embossed diffractive structures which include optical gratings, such as holographic or similar gratings that diffract the light into one or several diffraction orders (such gratings have characteristic periods between 500 nm and 10 microns) or also gratings with periods smaller than 500 nm's which enhance the absorption of a surface (antireflex gratings). Still further, the invention contemplates: a) complex random or semi-random nanostructures with sizes between 10 nm and 500 nm which significantly enhance the optical surface area of the pill and/or also trap the light leading to increased absorption and therefore darkening of the surface; b) tilted microstructures which reflect light into one or several directions. Such structures may for example be small pyramids or triangles with sizes somewhere in between of 2-500 microns; and c) flat, slightly grainy pill surface for enhanced reflectivity.

Figure 6A:
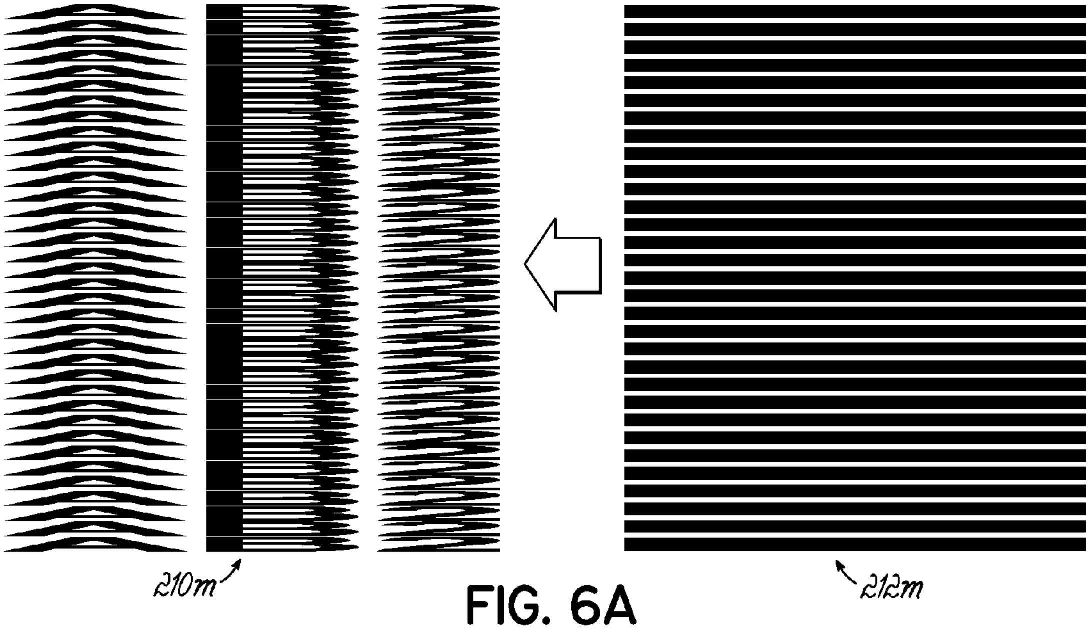
FIGS. 6A and 6B show another example of a Moiré pattern, according to the principles of the invention.
Figure 6B:
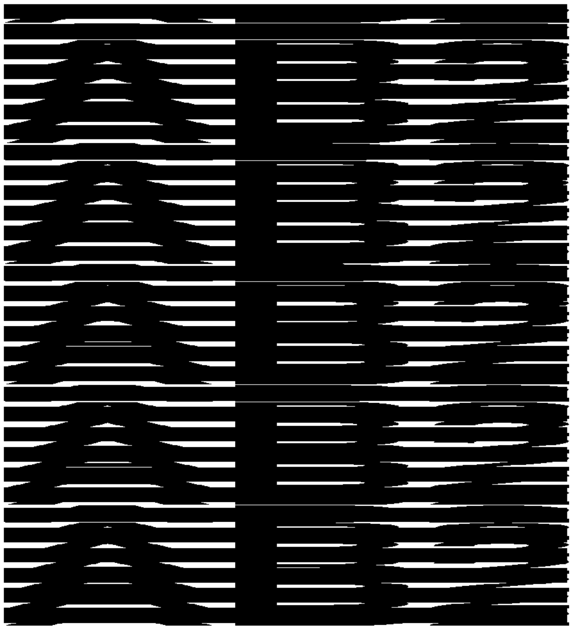

FIGS. 6A and 6B show another example of the Moiré effect, via a base layer 210, shown on the left, a revealing layer 212, shown on the right, and the Moiré pattern that is revealed when the revealing layer is superimposed over the base layer, as shown in FIG. 6B.

All such structures can be embossed during the manufacturing process of the pharmaceutical dosage form or pill, preferably by putting the negative of the structures into the surface of the pill-pressing tool and transferring the surface modification into the pill during the compaction process.

In order to get the desired moiré patterns, two or more of these different structures, or the same structure with different structure sizes or other structure characteristics, are combined laterally to form the base layer part of the moiré pattern on the pill surface.

Another possibility to make an image contrast with overcoatings is to emboss a structure with different heights into the core of the pill and then overcoat this structure with a layer whose surface is much flatter than the embossed structures. If the overcoating is thin and partly transparent, then the different thicknesses of the overcoating, caused by the underlying embossed structure, will be made visible as, e.g., a color difference (if the overcoating is colored) or as, e.g., differences in opaqueness.

Superposition of a regular pattern, squeezed in one direction with a corresponding revealing layer magnifies the direction again. Similar effects can also be achieved by combining random patterns (Glass pattern) or by a combination of random arrangements with identical microstructures.

Many different optical illusions can be created with solid pharmaceutical dosage forms using moiré patterns, among others these include:

moiré-magnification (see FIG. 6)

Glass patterns moiré speed-up revelation of hidden patterns creating illusions of movement While this application describes several preferred embodiments of the invention, those skilled in the art will readily appreciate that the described embodiments are merely exemplary in nature, and that the subject matter is not limited to that which is expressly shown or described. Accordingly, applicants wish to be bound by the claims, not the particular details described herein.

We claim:

1. A pharmaceutical dosage form combination with reduced susceptibility to counterfeiting, comprising: a pharmaceutical dosage form including a surface or interface; a Moiré pattern base layer formed directly on the surface or interface of the pharmaceutical dosage form such that the base layer cannot be removed from the pharmaceutical dosage form without destroying the base layer and the pharmaceutical dosage form; and a Moiré pattern revealing layer through which the pharmaceutical dosage form may be viewed, the revealing layer being separable from the pharmaceutical dosage form, wherein the Moiré pattern base layer and the Moiré pattern revealing layer form a Moiré pair that produces a contrast visible to the human eye and wherein a Moiré effect is seen by an observer by looking through the revealing layer, when the revealing layer is positioned relative to and spaced from the base layer.

2. The pharmaceutical dosage form combination of claim 1, wherein the revealing layer is formed on a transparent material.

3. The pharmaceutical dosage form combination of claim 2 wherein the observed Moiré effect occurs when the revealing layer is positioned close to and in alignment with the base layer.

4. The pharmaceutical dosage form combination of claim 1, further comprising:

a coating covering the pharmaceutical dosage form and the Moiré pattern base layer.

5. The pharmaceutical dosage form combination of claim 1, further comprising:

at least one part of a package serving as the Moiré pattern revealing layer, such that the Moiré effect is observable through the at least one part of the package when the pharmaceutical dosage form resides on an opposite side thereof.

6. The pharmaceutical dosage form combination of claim 5, wherein the Moiré effect is observable when the pharmaceutical dosage form resides in the package.

7. A pharmaceutical dosage form combination with reduced susceptibility to counterfeiting, made according to the following process: forming a Moiré pattern base layer directly on a surface or interface of a pharmaceutical dosage form such that the base layer cannot be removed from the pharmaceutical dosage form without destroying the base layer and the pharmaceutical dosage form; and providing a Moiré pattern revealing layer that is separable from the pharmaceutical dosage form, the pharmaceutical dosage form being viewable through the revealing layer, wherein the Moiré pattern base layer and the Moiré pattern revealing layer form a Moiré pair that produces a contrast visible to the human eye such that a Moiré effect is observable when looking through the revealing layer, when the revealing layer is positioned relative to and spaced from the base layer.

8. The pharmaceutical dosage form combination of claim 7, wherein the process further comprises:

forming the Moiré pattern base layer in the pharmaceutical dosage form by embossing.

9. The pharmaceutical dosage form combination of claim 7, wherein the process further comprises:

providing the Moiré pattern revealing layer on a transparent material.

10. The pharmaceutical dosage form combination of claim 9 wherein the observed Moiré effect occurs when the revealing layer is positioned close to and in alignment with the base layer.

11. The pharmaceutical dosage form combination of claim 1, wherein the revealing layer is provided by an electronic camera system that operates to image the base layer and to electronically superimpose the revealing layer onto the image of the base layer to reveal the Moiré pattern.

12. The pharmaceutical dosage form combination of claim 7, wherein the process further comprises:

providing the Moiré pattern revealing layer on an electronic camera system that images the base layer and electronically superimposes the revealing layer onto the image of the base layer to reveal the Moiré pattern.

13. The pharmaceutical dosage form combination of claim 7, wherein the process further comprises:

providing the Moiré pattern revealing layer on at least one part of a package configured to contain the pharmaceutical dosage form.

* * * * *